United States Patent [19]

Kroushl et al.

[11] 4,411,870

[45] Oct. 25, 1983

[54] REACTOR SYSTEM

[75] Inventors: Joseph A. Kroushl, Westchester; Arthur R. Greenwood, Niles, both of Ill.

[73] Assignee: UOP Inc., Des Plaines, Ill.

[21] Appl. No.: 470,429

[22] Filed: Feb. 28, 1983

Related U.S. Application Data

[63] Continuation-in-part of Ser. No. 334,503, Dec. 28, 1981.

[51] Int. Cl.³ .............................................. B01J 8/12
[52] U.S. Cl. ................................... 422/188; 208/169; 422/197; 422/216; 422/218
[58] Field of Search .............. 422/188, 216, 218, 220, 422/141, 145, 191–197, 236–239; 48/214 A; 208/138, 169; 55/474, 479; 203/29, 41; 201/34; 202/262

[56] References Cited

U.S. PATENT DOCUMENTS

| | | | |
|---|---|---|---|
| 1,982,099 | 11/1934 | Hechenbleikner | 422/218 X |
| 2,617,718 | 11/1952 | Miller | 422/218 |
| 2,683,654 | 7/1954 | Bergman | 422/218 |
| 3,594,131 | 7/1971 | De Palma et al. | 422/218 |
| 3,620,685 | 11/1971 | Rogers et al. | 422/192 |
| 3,692,496 | 9/1972 | Greenwood et al. | 422/191 |
| 3,725,248 | 4/1973 | Greenwood et al. | 208/138 |
| 3,882,015 | 5/1975 | Carson | 208/169 |
| 3,918,930 | 11/1975 | Forbes et al. | 48/214 A |
| 4,040,794 | 8/1977 | Stone | 422/216 X |
| 4,135,886 | 1/1979 | Kuchar | 422/218 X |

Primary Examiner—Richard L. Chiesa
Attorney, Agent, or Firm—James R. Hoatson, Jr.; John F. Spears, Jr.; William H. Page, II

[57] ABSTRACT

A reactor system is disclosed which comprises a reaction chamber containing a plurality of reaction zones, each of which comprises an annular-form catalyst-retaining section, whereby a reactant stream is distributed amongst said reaction zones in a manner to promote uniform flow of reactants across said sections. The disclosed reactor system is of particular advantage with respect to a relatively low pressure hydrocarbon conversion process.

20 Claims, 2 Drawing Figures

REACTOR SYSTEM

CROSS-REFERENCE TO RELATED APPLICATION

This application is a continuation-in-part of our prior copending application Ser. No. 334,503 filed on Dec. 28, 1981. The entire teaching of our prior application is hereby incorporated herein by reference.

BACKGROUND OF THE INVENTION

The present invention relates to a reactor system and process which is particularly useful in the vapor phase conversion of various hydrocarbon feedstocks. The reactor system provides radial flow contact of a reactant stream with catalyst particles contained in a fixed annular-form bed, or movable as an annular-form bed through said reactor system via gravity flow. The reactor system is adapted to a single stage hydrocarbon conversion process wherein a reactant stream is processed through a single reaction chamber in contact with catalyst particles contained therein, or to a multiple stage hydrocarbon conversion process wherein a reactant stream is processed serially through two or more reaction chambers in contact with catalyst particles which are preferably movable serially through said reaction chamber via gravity flow, said reaction chamber being arranged in stacked or side-by-side configuration or a combination thereof.

Various vapor phase conversion processes have heretofore been effected utilizing a reactor system wherein a reactant stream is processed in radial flow through a vertically positioned annular-form catalyst bed—an arrangement that offers many design and operating advantages, particularly with respect to those vapor phase processes for the conversion of hydrocarbons. Illustrative of a reactor system wherein a reactant stream is caused to flow laterally and radially through an annular-form catalyst bed is that described in U.S. Pat. No. 2,683,654. The reactor system illustrated is intended for a fixed bed operation. A reactant stream charged to a reaction chamber flows from an outer annular-form space created between the chamber walls and the annular-form catalyst bed, said stream flowing laterally and radially through said catalyst bed and into a perforated centerpipe to be discharged from the reaction chamber. U.S. Pat. No. 3,692,496 describes a somewhat related reactor system in that a reactant stream charged to a reaction chamber is caused to flow laterally and radially from an outer annular-form space through an annular-form catalyst section and into an inner or center manifold to be discharged from said chamber. In the latter case, the reactor system comprises stacked reaction chambers (and consequently stacked annular-form catalyst sections) designed to process catalyst particles downwardly via gravity flow from one annular-form catalyst section through the next lower annular-form catalyst section, the catalyst particles being recovered from the lowermost reaction chamber for regeneration. A variation of the last described reactor system appears in U.S. Pat. No. 3,725,248 wherein the annular-form catalyst sections are individually contained in side-by-side reaction chambers, and in U.S. Pat. No. 3,882,015 wherein the reactant stream is reversed to flow laterally and radially from a center reactant conduit through an annular-form catalyst section and into an outer annular-form space formed by the annular-form catalyst section and the reaction chamber walls.

In addition to the foregoing reactor systems in which the reactant stream is processed laterally and radially across an annular-form catalyst bed, reactor systems comprising multiple catalyst beds in a single reactor vessel have been utilized. For example, U.S. Pat. No. 4,040,794 discloses a reactor wherein the reactants flow laterally and radially across and annular-form moving catalyst bed. However, this reactor system also employs baffles attached along the sides of the annular-form catalyst bed to channel reactant flow in such a manner as to create several distinct serially connected catalyst beds from a single bed of catalyst within one reactor vessel. U.S. Pat. No. 2,617,718 discloses a further reactor system of the stationary type comprising a reactor housing with a plurality of catalyst containers located therein. The catalyst containers are depicted as annular-form catalyst beds emplaced within foraminous containers. The inlet and outlet baffles as well as the emplacement of the catalyst containers act to channel reactant flow in such a manner as to create a plurality of catalyst beds in parallel arrangement. In addition, there are baffles situated around and within each catalyst container to promote uniform flow of reactants across the annular-form catalyst beds.

The foregoing reactor systems have heretofore been described with respect to vapor phase conversion processes wherein they are employed to effect a number of catalyst-promoted conversions. Prominent among such conversion processes are the hydrocarbon conversion processes and include catalytic reforming, hydrogenation, hydrocracking, hydrorefining, isomerization, and dehydrogenation, as well as alkylation, transalkylation, steam reforming, and the like. The reactor system of the present invention can be similarly employed but is of particular advantage with respect to a relatively low pressure operation, such as propane and/or butane dehydrogenation at near-atmospheric pressures.

BRIEF SUMMARY OF THE INVENTION

The reactor system of the present invention provides for the containment of catalyst particles within a plurality of annular-form catalyst sections contained in a reaction chamber whereby a reactant stream is distributed amongst said plurality of catalyst sections to effect a minimal pressure drop—a feature which is of particular advantage with respect to a relatively low pressure hydrocarbon conversion process. Briefly, the reactor system of this invention comprises two or more vertically positioned annular-form catalyst-retaining sections existing side-by-side in a reaction chamber, each of said catalyst-retaining sections being defined by an inner tubular-form catalyst-retaining screen (typically supported by a perforated or slotted centerpipe) coaxially disposed within a vertically positioned outer tubular-form catalyst-retaining screen. Catalyst particles are preferably movable through the resulting annular-form catalyst sections in a dense phase via gravity flow. The reactant stream may be introduced into the reaction chamber and distributed into each of said annular-form catalyst-retaining sections by way of a fluid flow conduit created by the inner catalyst-retaining screen, the reactant stream then being in each case directed outwardly from said conduit, through the annular-form catalyst-retaining section in a substantially radial flow, and into the reaction chamber void space to be recovered in admixture with the effluent from the other annular-form catalyst-retaining sections contained therein. Alternatively, the reactant stream may be introduced into the reaction chamber void space and distributed into each of said annular-form catalyst-retaining sections across the outer catalyst-retaining screen, the reactant stream being in each case directed inwardly from said outer catalyst screen, through the annular-form catalyst-retaining section in a substantially radial flow, and into the fluid flow conduit defined by the inner catalyst-retaining screen to be recovered in admixture with the effluent from the other reaction chamber annular-form catalyst-retaining sections by way of a manifold. Additionally the reaction chamber of the present invention has associated therewith first and second ports both located in one of said extremities. The first and second ports serve as means for introducing reactants to the reaction chamber and as means for withdrawing the reaction effluents. It should be noted that, in contrast to the reactor system of the present invention, the reactor systems previously described do not employ a plurality of catalyst-retaining sections in a single reaction chamber in conjunction with the advantageous location of the reactant and reaction effluent ports.

DETAILED DESCRIPTION OF THE INVENTION

Figure 1:
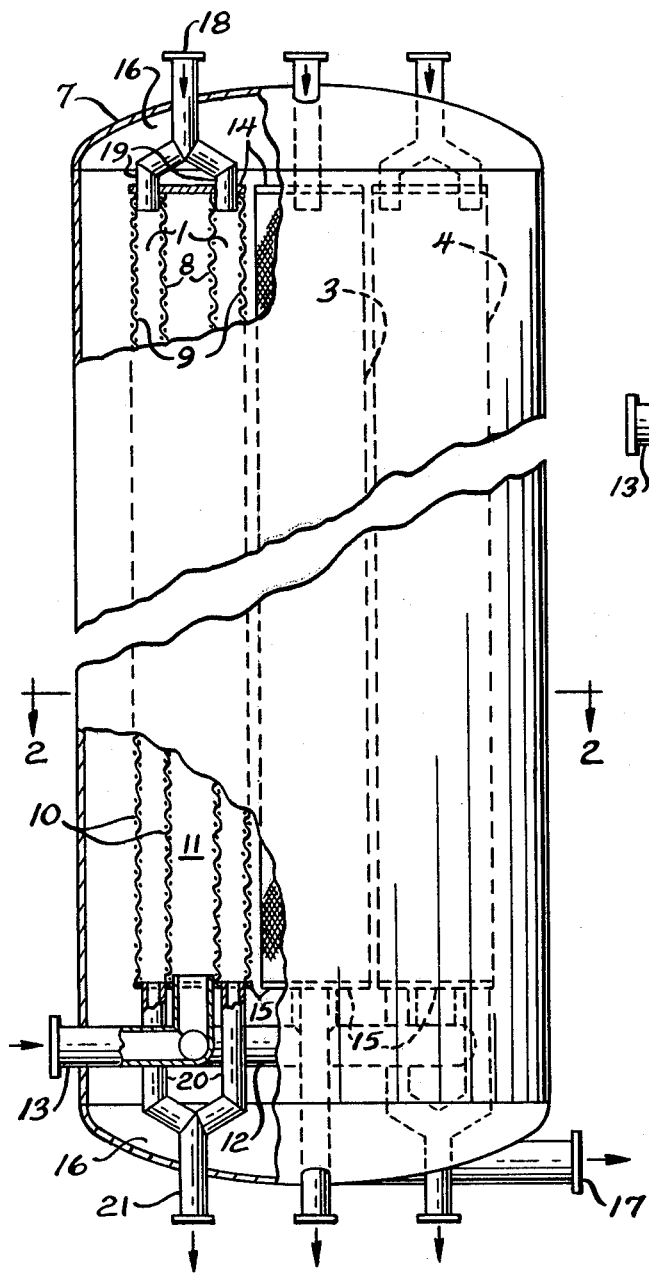

In one of its broad aspects, the present invention embodies a reactor system which comprises, in combination, a vertically elongated confined reaction chamber having upper and lower extremities; a first port and a second port associated with the chamber, both located in one of said extremities; said chamber containing a plurality of side-by-side annular-form vertically aligned catalyst-retaining sections positioned therein; each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof; said chamber containing a first flow manifold connecting said first port to one extremity of each of said fluid flow conduits; each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen; and, said chamber having a void space in open communication with said second port, and defined by the inner walls of the chamber and the outer surface of the plurality of catalyst-retaining sections contained therein, said void space serving as a second flow manifold connecting the outer surface of the plurrality of catalyst-retaining sections to the second port.

One of the more specific embodiments concerns a reactor system which comprises, in combination, a vertically elongated confined reaction chamber having upper and lower extremities; a first port and a second port associated with the chamber, both located in one of said extremities; said chamber containing a plurality of side-by-side annular-form vertically aligned catalyst-retaining sections positioned therein; each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof; said chamber containing a first flow manifold connecting said first port to one extremity of each of said fluid flow conduits; each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen; and said chamber having a void space in open communication with said second port, and defined by the inner walls of the chamber and the outer surface of the plurality of catalyst-retaining sections contained therein, said void space serving as a second flow manifold connecting the outer surface of the plurality of catalyst-retaining sections to the second port, said reaction chamber further comprising catalyst supply conduits extending downwardly through the upper extremity thereof and in open communication with the upper extremity of each of said annular-form catalyst-retaining sections, and catalyst recovery conduits in open communication with the lower extremity of each of said annular-form catalyst-retaining sections and extending downwardly through the lower extremity of said reaction chamber.

In another aspect, the invention broadly embodies a process for the conversion of a hydrocarbon charge stock characterized in that the hydrocarbon charge stock is passed in vapor phase to a reactor system comprising, in combination, a vertically elongated confined reaction chamber having upper and lower extremities; a first port and a second port associated with the chamber, both located in one of said extremities; said chamber containing a plurality of side-by-side annular-form vertically aligned catalyst-retaining sections positioned therein; each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof; said chamber containing a first flow manifold connecting said first port to one extremity of each of said fluid flow conduits; each of said catalyst-retaining sections being further defined by two transverse partitions, one connected to the upper extremity of said fluid flow conduit and to the upper perimeter of said outer catalyst-retaining screen, and the outer connected to the lower extremity of said fluid flow conduit and to the lower perimeter of said outer catalyst-retaining screen; and said chamber having a void space in open communication with said second port, and defined by the inner walls of the chamber and the outer surface of the plurality of catalyst-retaining sections contained therein, said void space serving as a second flow manifold connecting the outer surface of the plurality of catalyst-retaining sections to the second port.

In a further embodiment of the process of the invention, the hydrocarbon feedstock is subjected to catalytic dehydrogenation in the reactor system in the presence of a dehydrogenation catalyst emplaced within the catalyst-retaining sections.

The further description of the reactor system and process of the present invention is presented with reference to the attached schematic drawing.

FIG. 1 of the drawing represents a side view of a reactor system in accordance with the present invention which is partially broken away and sectioned.

Figure 2:
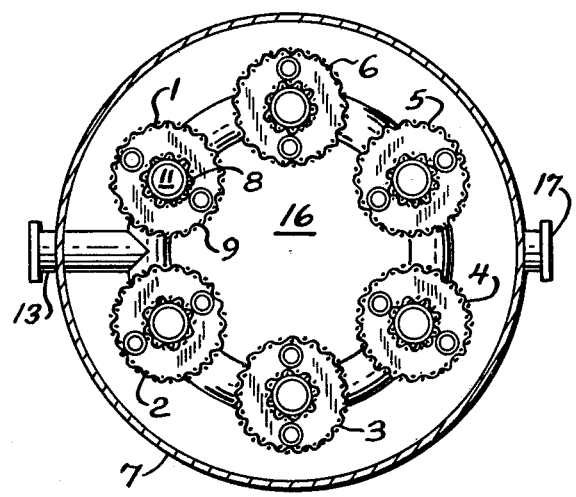

FIG. 2 is a sectional view of the reactor system looking down from the upper portion of the reaction chamber.

The drawing is presented in illustration of one preferred embodiment of the invention and is not intended as an undue limitation on the generally broad scope of the invention as set out in the appended claims. While the drawing depicts a first flow manifold connecting a first port to the lower extremity of each of a plurality of fluid flow conduits, as well as a second port at the lower extremity of the reaction chamber, it is understood that said flow manifold may be connected to the upper extremity of each of said fluid flow conduits and to the first port with said first and second ports being then located in the upper extremity of the reaction chamber.

Additionally, even though reactant flow across each catalyst-retaining section is depicted as being from the fluid flow conduit radially outward toward the outer catalyst-retaining screen, the flow pattern through the reactor system may be advantageously reversed depending on the specific application. Hence reactant flow across the catalyst-retaining sections may be radially inward from the outer catalyst-retaining screen toward the fluid flow conduit. Also, while a reactant stream is depicted as being processed through a reactor system comprising a single reaction chamber, it is understood that the reactor system may comprise two or more vertically stacked reaction chambers, or the reactor system may comprise two or more reaction chambers arranged side-by-side, provision being made in either case for intermediate heating of a reactant stream between said chambers to maintain a desired reaction temperature in the various chambers. In the multiple stage or multiple reaction chamber system, fresh and/or regenerated catalyst particles may be added continuously or intermittently to an initial or top reaction chamber and processed serially or sequentially through the reactor system, said particles being withdrawn from the final or bottom reaction chamber, as the case may be, for subsequent regeneration. Also, the reactor system of this invention may comprise two or more side-by-side reaction chambers whereby fresh and/or regenerated catalyst particles may be added continuously or intermittently to each of two or more reaction chambers, the catalyst particles being withdrawn from each of said reaction chambers to be regenerated separately or in combination. Alternatively, the catalyst particles of a selected reaction chamber may be regenerated periodically while maintaining all reaction chambers, including the selected reaction chamber, onstream at hydrocarbon conversion conditions. In the preferred reactor system comprising stacked reaction chambers, the reactor system will in effect comprise a plurality of annular-form catalyst beds, each of which is movable downwardly from the top reaction chamber and through the reactor system as substantially unbroken or continuous annular-form columns to be recovered from the bottom reaction chamber. Thus, all reaction chambers are maintained onstream while fresh and/or regenerated catalyst particles are added to the top reaction chamber, and used catalyst particles are recovered from the bottom reaction chamber to effect a substantially continuous process.

Referring then to the drawing, there are shown six annular-form vertically aligned catalyst-retaining sections numbered 1, 2, 3, 4, 5 and 6, circumferentially spaced within a reaction chamber 7, all of said catalyst-retaining sections being visible in a sectional top view, FIG. 2. Catalyst-retaining sections 1, 3 and 4 are visible in a sectional plan view, FIG. 1, with catalyst-retaining section 2 and those sections in vertical alignment therewith being not shown to provide a more complete view of first flow manifold 12. The six catalyst-retaining sections are preferably circumferentially spaced as this arrangement permits ready access to each for repair or replacement should the occasion arise. Otherwise, from four to seven catalyst-retaining sections are preferred per reaction chamber. All of said catalyst-retaining sections being substantially identical, the description of catalyst-retaining section 1 will serve to also describe the remaining sections. With reference then to catalyst-retaining section 1, said section comprises an inner tubular-form catalyst-retaining screen 8 coaxially disposed within a vertically positioned outer tubular-form catalyst-retaining screen 9. Both the inner and outer catalyst-retaining screen members comprise perforations 10. The inner tubular-form catalyst-retaining screen 8 further defines a fluid flow conduit 11 within the inner space thereof. A first flow manifold 12 is connected to the lower extremity of each of the fluid flow conduits 11 whereby a reactant stream introduced into the reaction chamber 7 by way of first port 13 is distributed into each of said catalyst-retaining sections. Transverse partition 14 is connected to the upper extremity of fluid flow conduit 11 and to the upper perimeter of outer catalyst-retaining screen 9 while transverse partition 15 is connected to the lower extremity of fluid flow conduit 11 and the lower perimeter of outer catalyst-retaining screen 9. A reactant stream rising through fluid flow conduit 11 is thereby directed laterally and radially outward through annular-form catalyst-retaining section 1 and into void space 16 where the effluent from the plurality of catalyst-retaining sections is collected for discharge through second port 17 is open communication with void space 16. The void space 16 is defined by the interior walls of the reaction chamber 7 and the outer surface of the plurality of the catalyst-retaining screens contained therein. Of course as noted earlier, the flow pattern through the reactor system alternatively may be such that the reactant stream enters via second port 17 into void space 16 thereby flowing laterally and radially inward through annular-form catalyst-retaining section 1 and into fluid flow conduit 11 for eventual withdrawal via first flow manifold 12 and first port 13. Thus first port 13 may be an inlet or outlet port and second port 17 will correspondingly act as an outlet or inlet port. Fresh and/or regenerated catalyst particles are introduced through the upper extremity of the reaction chamber 7 by way of an inlet port 18. The catalyst particles gravitate downwardly through the catalyst conduit 19 which is in open communication with the upper extremity of the annular-form catalyst-retaining section 1. A plurality of conduit outlets into said annular-form catalyst-retaining section are circumferentially spaced to effect a substantially uniform distribution of catalyst particles thereto. The gravitating catalyst particles are withdrawn from the lower extremity of said annular-form catalyst-retaining section by means of catalyst recovery conduit 20. Transverse partition 15 directs catalyst particles, descending through the catalyst-retaining section, into said catalyst recovery conduit. The catalyst particles are recovered from reaction chamber 7 by way of outlet port 21, preferably for regeneration in an on-stream catalyst regeneration facility wherein the catalyst particles are treated as a gravitating moving bed in a continuous type of operation.

In the ebodiment depicted in the drawing, first port 13 and second port 17 are shown to be situated in the lower extremity of reaction chamber 7 and first flow manifold 12 correspondingly connects first port 13 to the lower extremity of fluid flow conduit 11. Alternatively, both ports may be situated in the upper extremity of the reaction chamber. When both ports are so located, first flow manifold 12 will then correspondingly connect first port 13 to the upper extremity of the fluid flow conduits. By connecting first flow manifold 12 to the extremity of the fluid flow conduits which correspond to the reaction chamber extremity in which first port 13 and second port 17 are located, two major advantages result. First, the amount of internal conduit comprising the first flow manifold is minimized thereby resulting in reduced cost and lower pressure drop through the reaction chamber. Second, the velocity heads of the vapor in the fluid flow conduits and in the void space surrounding the catalyst-retaining sections become balanced thereby promoting a more uniform flow of vapor across the length of the catalyst-retaining sections. The vapor velocity heads become balanced as a result of the vapor flow path through the fluid flow conduits and through the reaction chamber void space. The velocity head of the vapor decreases as the vapor passes along the length of the fluid flow conduit. Accordingly, then, the vapor velocity head is at a maximum at the inlet to the fluid flow conduit and is essentially zero at the terminal end (the upper end in FIG. 1) thereof. As the velocity head of the vapor decreases, the pressure of the vapor increases. Therefore, the vapor pressure at the fluid flow conduit inlet is less than the vapor pressure at the terminal end of the fluid flow conduit and there accordingly exists a vapor pressure gradient along the fluid flow conduit from the inlet to the terminal end thereof. In order to assure uniform flow of vapor across the catalyst beds contained in the annular catalyst-retaining sections, a corresponding vapor pressure gradient must be induced in the void space and therefore, the vapor velocity head in the void space must correspondingly decrease in the same direction as that in the fluid flow conduit to assure a corresponding vapor pressure gradient on the void space side of the catalyst-retaining sections. The vapor flow in the void space must be such that a minimum vapor velocity head therein occurs at a point corresponding to the terminal end of fluid flow conduits and a maximum vapor velocity head therein occurs at a point corresponding to the inlet of the fluid flow conduits. Such a vapor flow will occur in the void space if the flow of vapor therein is in the opposite direction to the flow of vapor in the fluid flow conduit. If, contrary to the above, the vapor flow in the void space is in the same direction as that in the fluid flow conduit, the vapor pressure gradient in the void space will be the opposite of that in the fluid flow conduit and will result in nonuniform flow of vapor across the annular catalyst bed. Accordingly then, the advantages to be derived by situating the first port and the second port in the same extremity of the reaction chamber become apparent. By so situating the ports, it is possible to induce vapor flow patterns through the void space and the fluid flow conduits which result in a more uniform flow of vapor across the annular catalyst bed. Moreover, the improvement in the uniformity of vapor flow will be achieved regardless of whether the first port and second port are both located in the upper or lower extremity of the reaction chamber or whether the flow is outward from the fluid flow conduits to the void space or inward from the void space to the fluid flow conduits.

The reactor system of the present invention is of particular advantage with respect to the conversion of hydrocarbons and in particular the dehydrogenation of hydrocarbons in the presence of a dehydrogenation catalyst—an established and well known hydrocarbon conversion process in the petroleum refining industry. The invention offers special advantage when the hydrocarbon charge stock to be dehydrogenated comprises $C_2+$ normally gaseous hydrocarbons with the desired product comprising the corresponding monoolefins. The monoolefinic products are generally useful as intermediates in the production of other more valuable products, and the catalytic dehydrogenation process is typically utilized in conjunction with various other hydrocarbon conversion processes to yield a desired final product. For example, utilizing liquid petroleum gas (LPG)—a compressed or liquefied gas consisting of propane and butane or mixed butanes—as a starting material, catalytic dehydrogenation can be utilized to produce propylene and/or butylenes in conjunction with an HF alkylation unit wherein said olefins are alkylated with isobutane to produce a high octane motor fuel; or in conjunction with a catalytic condensation unit wherein said olefins are condensed to form tetramers or polymer gasoline; or in conjunction with an etherification unit wherein isobutylene is reacted with methanol to produce methyl t-butyl ether, a highly desirable gasoline additive.

The catalytic dehydrogenation process will preferably utilize a catalytic composite comprising a platinum group metal component, a tin component, and an alkali metal component composited with a porous, high surface area, adsorbent support or carrier material. Of the platinum group metals, i.e., platinum, palladium, ruthenium, rhodium, osmium and iridium, platinum is a preferred catalyst component. The platinum component will generally comprise from about 0.01 to about 2.0 wt.% of the catalytic composite, and the tin component will generally comprise from about 0.01 to about 5 wt.% thereof. Of the alkali metals, i.e., cesium, rubidium, potassium, sodium and lithium, lithium and/or potassium are preferred. The alkali metal will generally constitute from about 0.1 to about 3.5 wt.% of the catalytic composite. One preferred catalytic composite comprises from about 0.1 to about 1.0 wt.% platinum, and from about 0.1 to about 1.0 wt.% tin and from about 0.2 to about 3.0 wt.% lithium or potassium composited with a porous adsorbent support or carrier material having a surface area of from about 25 to about 500 m$^2$/g. The preferred carrier materials are the refractory inorganic oxides with best results being obtained with an alumina support or carrier material.

The catalytic dehydrogenation process herein contemplated is a relatively high temperature operation effected at a temperature of from about 900° to about 1300° F., and preferably from about 1000° to about 1250° F. The process is also a relatively low pressure operation effected at a pressure of from about 0 to about 35 psig, preferably from about 10 to about 30 psig. The reactor system of this invention is of still further advantage with respect to the relatively high temerature operation in that the flow pattern may be such that the reactants have minimal exposure to thermal conversion conditions prior to contact with the dehydrogenation catalyst to substantially obviate conversion to other than the desired dehydrogenation products. This is accomplished by distributing the inlet reactant stream directly into each of the fluid flow conduits formed by the inner catalyst-retaining screens thereby creating a reactant flow path outward from the fluid flow conduits. In this manner, the reactant stream is exposed to the high inlet temprature for a relatively brief period while it passes through the first flow manifold and the fluid flow conduits. While the residence time of the reactant stream in the relatively high capacity void space outside of the annular-form catalyst beds is substantially longer, thermal conversion is negligible because of the drop in reactant stream temperature resulting from the endothermic nature of the dehydrogenation reaction.

The reactor system of this invention is of particular advantage with respect to the relatively low pressure operation in that it allows a high throughput with minimal pressure drop. This results from the multiple annular-form catalyst-retaining sections employed herein as opposed to the more conventional unitary annular-form catalyst-retaining sections. Generally from four to seven catalyst-retaining sections per reaction chamber in the process of the invention with six being preferred. Each catalyst-retaining section provides an overall annular-form catalyst bed having a larger cross-sectional area allowing for a relatively shallow catalyst bed. The radially flowing reactant stream thus experiences a minimal pressure drop across the bed. In addition, the relatively low pressure drop facilitates the gravitational flow of catalyst particles through the multiple annular-form catalyst-retaining sections.

Notwithstanding that the catalytic dehydrogenation process involves hydrogen-producing reactions, it has been the practice to charge hydrogen to the reaction zone, typically recycle hydrogen, in admixture with the hydrocarbon feedstock—a practice which has been found to promote catalyst activity as well as activity-stability. Dehydrogenation conditions thus further include a hydrogen to hydrocarbon mole ratio of from about 1 to about 10, and more suitably from about 1 to about 4. The hydrocarbon reactant stream is also suitably charged at a rate to provide a liquid hourly space velocity of from about 2 to about 6.

We claim as our invention:
1. A reactor system comprising, in combination:
   (a) a vertically elongated confined reaction chamber having upper and lower extremities;
   (b) a first port and a second port associated with the chamber, both located in one of said extremities;
   (c) said chamber containing a plurality of side-by-side annular-form vertically aligned catalyst-retaining sections positioned therein;
   (d) each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit within the inner space thereof;
   (e) said chamber containing a first flow manifold connecting said first port to one extremity of each of said fluid flow conduits;
   (f) each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen; and,
   (g) said chamber having a void space in open communication with said second port, and defined by the inner walls of the chamber and the outer surface of the plurality of catalyst-retaining sections contained therein, said void space serving as a second flow manifold connecting the outer surface of the plurality of catalyst-retaining sections to the second port.

2. The reactor system of claim 1 further characterized in that said reaction chamber further comprises catalyst supply conduits extending donwardly through the upper extremity thereof and in open communication with an upper extremity of each of said annular-form catalyst-retaining sections, and catalyst recovery conduits in open communication with a lower extremity of each of said annular-form catalyst-retaining sections and extending downwardly through the lower extremity of said reaction chamber.

3. The reactor system of claim 1 further characterized in that said reaction chamber contains from four to seven of said side-by-side annular-form vertically aligned catalyst-retaining sections.

4. The reactor system of claim 3 further characterized in that said reaction chamber contains six of said side-by-side annular-form vertically aligned catalyst-retaining sections circumferentially spaced therein.

5. The reactor system of claim 1 further characterized in that said first flow manifold connects the first port with a lower extremity of each of said fluid flow conduits.

6. The reactor system of claim 5 further characterized in that said first and second ports are located at the lower extremity of said reaction chamber.

7. The reactor system of claim 1 further characterized in that said first flow manifold connects the first port with an upper extremity of each of said fluid flow conduits.

8. The reactor system of claim 6 further characterized in that said first and second ports are located at the upper extremity of said reaction chamber.

9. The reactor system of claim 1 further characterized in that said first port is a reactant inlet port and said second port is a reaction effluent outlet port.

10. The reactor system of claim 1 further characterized in that said first port is a reaction effluent outlet port and said second port is a reactant inlet port.

11. A process for the conversion of a hydrocarbon charge stock characterized in that the hydrocarbon charge stock is passed in vapor phase to a reactor system comprising, in combination:
   (a) a vertically elongated confined reaction chamber having upper and lower extremities;
   (b) a first port and a second port associated with the chamber, both located in one of said extremities;
   (c) said chamber containing a plurality of side-by-side annular-form vertically aligned catalyst-retaining sections positioned therein;
   (d) each of said catalyst-retaining sections being defined by an inner tubular-form catalyst-retaining screen coaxially disposed within an outer vertically positioned tubular-form catalyst-retaining screen, said inner catalyst-retaining screen further defining a fluid flow conduit the inner space thereof;

(e) said chamber containing a first flow manifold connecting said first port to one extremity of each of said fluid flow conduits;

(f) each of said catalyst-retaining sections being further defined by two transverse partitions, one connected to the upper extremity of said fluid flow conduit and to the upper perimeter of said outer catalyst-retaining screen, and the other connected to the lower extremity of said fluid flow conduit and to the lower perimeter of said outer catalyst-retaining screen; and, (g) said chamber having a void space in open communication with said second port, and defined by the inner walls of the chamber and the outer surface of the plurality of catalyst-retaining sections contained therein, said void space serving as a second flow manifold connecting the outer surface of the plurality of catalyst-retaining sections to the second port.

12. The process of claim 11 further characterized in that said hydrocarbon feedstock is subjected to catalytic dehydrogenation in the reactor system in the presence of a dehydrogenation catalyst emplaced within the catalyst-retaining sections.

13. The process of claim 12 further characterized in that said hydrocarbon charge stock comprises $C_2+$ normally gaseous hydrocarbons.

14. The process of claim 13 further characterized in that the hydrocarbon charge stock comprises propane or butane.

15. The process of claim 11 further characterized in that said reaction chamber contains from four to seven of said side-by-side annular-form vertically aligned catalyst-retaining sections.

16. The process of claim 15 further characterized in that said reaction chamber contains six of said side-by-side annular-form vertically aligned catalyst-retaining sections circumferentially spaced therein.

17. The process of claim 11 further characterized in that said first and second ports are located at the lower extremity of said reaction chamber.

18. The process of claim 11 further characterized in that said reaction chamber further comprises catalyst supply conduit extending downwardly through the upper extremity thereof and in open communication with an upper extremity of each of said annular-form catalyst-retaining sections, and catalyst recovery conduit in open communication with a lower extremity of each of said annular-form catalyst-retaining sections and extending downwardly through the lower extremity of said reaction chamber.

19. The process of claim 11 further characterized in that said first port is a hydrocarbon charge stock inlet port and said second port is a reaction effluent outlet port.

20. The process of claim 11 further characterized in that said second port is a hydrocarbon charge stock inlet port and said first port is a reaction effluent outlet port.

* * * * *